(12) United States Patent
Broun et al.

(10) Patent No.: US 7,241,868 B1
(45) Date of Patent: Jul. 10, 2007

(54) CRYSTALLIZATION OF GLUCOCORTICOID RECEPTOR

(75) Inventors: Alexei Broun, San Diego, CA (US);
Oleg Brodsky, San Diego, CA (US);
Ellen Chien, La Jolla, CA (US);
Douglas R. Dougan, Calgary (CA);
Clifford D. Mol, San Diego, CA (US);
Gyorgy Snell, Richmond, CA (US)

(73) Assignee: Takeda San Diego, Inc., San Diego, CA (US)

( * ) Notice: Subject to any disclaimer, the term of this patent is extended or adjusted under 35 U.S.C. 154(b) by 135 days.

(21) Appl. No.: 10/960,642

(22) Filed: Oct. 6, 2004

(51) Int. Cl.
*C07K 14/00* (2006.01)

(52) U.S. Cl. .................................................. 530/350

(58) Field of Classification Search ............. None
See application file for complete search history.

(56) References Cited

OTHER PUBLICATIONS

Creighton. T., "Encyclopedia of Molecular Biology", John Wiley and Sons, Inc. New York, 1999, pp. 586 and 2725.*
Weber, P.C. Overview of Crystallization Methods. Methods in Enzymology, 1997, vol. 276, pp. 13-22.*
Drenth, J. "Principles of Protein X-Ray Crystallography", 2nd Edition, 1999 Springer-Verlag New York Inc., Chapter 1, pp. 1-19.*
Cudney, R. Protein Crystallization and Dumb Luck. Rigaku Journal. 1999. vol. 16, No. 1, pp. 1-7.*
Bledsoe et al. Crystal Structure of the Glucocorticoid Receptor Ligand Binding Domain Reveals a Novel Mode of Receptor Dimerization and Coactivator Recognition. Cell. Jul. 2002. vol. 110, pp. 93-105.*
Sequence alignment of Bledsoe et al. crystal sturcture sequence from pdb file 1M2Z and SEQ ID No. 1 528-777.*

* cited by examiner

*Primary Examiner*—Kathleen Kerr Bragdon
*Assistant Examiner*—Suzanne M. Noakes
(74) *Attorney, Agent, or Firm*—David J. Weitz (57) ABSTRACT

Provided are crystals relating to human Glucocorticoid Receptor and its various uses.

9 Claims, 3 Drawing Sheets

FIGURE 1

Amino acid sequence for human Glucocorticoid Receptor [SEQ. ID No. 1]

(Residues 528-777 are underlined)

```
  1  MDSKESLTPG REENPSSVLA QERGDVMDFY KTLRGGATVK VSASSPSLAV
 51  ASQSDSKQRR LLVDFPKGSV SNAQQPDLSK AVSLSMGLYM GETETKVMGN
101  DLGFPQQGQI SLSSGETDLK LLEESIANLN RSTSVPENPK SSASTAVSAA
151  PTEKEFPKTH SDVSSEQQHL KGQTGTNGGN VKLYTTDQST FDILQDLEFS
201  SGSPGKETNE SPWRSDLLID ENCLLSPLAG EDDSFLLEGN SNEDCKPLIL
251  PDTKPKIKDN GDLVLSSPSN VTLPQVKTEK EDFIELCTPG VIKQEKLGTV
301  YCQASFPGAN IIGNKMSAIS VHGVSTSGGQ MYHYDMNTAS LSQQQDQKPI
351  FNVIPPIPVG SENWNRCQGS GDDNLTSLGT LNFPGRTVFS NGYSSPSMRP
401  DVSSPPSSSS TATTGPPPKL CLVCSDEASG CHYGVLTCGS CKVFFKRAVE
451  GQHNYLCAGR NDCIIDKIRR KNCPACRYRK CLQAGMNLEA RKTKKKIKGI
501  QQATTGVSQE TSENPGNKTI VPATLPQLTP TLVSLLEVIE PEVLYAGYDS
551  SVPDSTWRIM TTLNMLGGRQ VIAAVKWAKA IPGFRNLHLD DQMTLLQYSW
601  MFLMAFALGW RSYRQSSANL LCFAPDLIIN EQRMTLPCMY DQCKHMLYVS
651  SELHRLQVSY EEYLCMKTLL LLSSVPKDGL KSQELFDEIR MTYIKELGKA
701  IVKREGNSSQ NWQRFYQLTK LLDSMHEVVE NLLNYCFQTF LDKTMSIEFP
751  EMLAEIITNQ IPKYSNGNIK KLLFHQK
```

Human cDNA sequence encoding residues 528-777 of GR [SEQ. ID No. 2]

```
  1  CTCACCCCTA CCCTGGTGTC ACTGTTGGAG GTTATTGAAC CTGAAGTGTT ATATGCAGGA
 61  TATGATAGCT CTGTTCCAGA CTCAACTTGG AGGATCATGA CTACGCTCAA CATGTTAGGA
121  GGGCGGCAAG TGATTGCAGC AGTGAAATGG GCAAAGGCAA TACCAGGTTT CAGGAACTTA
181  CACCTGGATG ACCAAATGAC CCTACTGCAG TACTCCTGGA TGTTTCTTAT GGCATTTGCT
241  CTGGGGTGGA GATCATATAG ACAATCAAGT GCAAACCTGC TGTGTTTTGC TCCTGATCTG
301  ATTATTAATG AGCAGAGAAT GACTCTACCC TGCATGTACG ACCAATGTAA ACACATGCTG
361  TATGTTTCCT CTGAGTTACA CAGGCTTCAG GTATCTTATG AAGAGTATCT CTGTATGAAA
421  ACCTTACTGC TTCTCTCTTC AGTTCCTAAG GACGGTCTGA AGAGCCAAGA GCTATTTGAT
481  GAAATTAGAA TGACCTACAT CAAAGAGCTA GGAAAAGCCA TTGTCAAGAG GGAAGGAAAC
541  TCCAGCCAGA ACTGGCAGCG GTTTTATCAA CTGACAAAAC TCTTGGATTC TATGCATGAA
601  GTGGTTGAAA ATCTCCTTAA CTATTGCTTC CAAACATTTT TGGATAAGAC CATGAGTATT
661  GAATTCCCCG AGATGTTAGC TGAAATCATC ACCAATCAGA TACCAAAATA TTCAAATGGA
721  AATATCAAAA AACTTCTGTT TCATCAAAAG T
```

FIGURE 1 (Continued)

Amino acid sequence for residues 528-777 of GR with a N-terminal 6x-histidine tag, spacer region and thrombin cleavage site [SEQ. ID No. 3]
(6x-histidine tag, spacer region and thrombin cleavage site, and the two mutants F602S, W712S are underlined)

```
  1    MGSSHHHHHH  SSGLVPRGSH  MLTPTLVSLL  EVIEPEVLYA  GYDSSVPDST
 51    WRIMTTLNML  GGRQVIAAVK  WAKAIPGFRN  LHLDDQMTLL  QYSWMSLMAF
101    ALGWRSYRQS  SANLLCFAPD  LIINEQRMTL  PCMYDQCKHM  LYVSSELHRL
151    QVSYEEYLCM  KTLLLLSSVP  KDGLKSQELF  DEIRMTYIKE  LGKAIVKREG
201    NSSQNSQRFY  QLTKLLDSMH  EVVENLLNYC  FQTFLDKTMS  IEFPEMLAEI
251    ITNQIPKYSN  GNIKKLLFHQ  K
```

FIGURE 2

CRYSTALLIZATION OF GLUCOCORTICOID RECEPTOR

FIELD OF THE INVENTION

The present invention relates to a member of a family of nuclear hormone receptors and more specifically to a particular nuclear hormone receptor known as GLUCOCORTICOID RECEPTOR (GR). Provided are GR in crystalline form, methods of forming crystals comprising GR, and methods of using crystals comprising GR.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein. A need thus exists for proteins in crystalline form.

SUMMARY OF THE INVENTION

The present invention is directed to crystals comprising GR and particularly crystals comprising GR that have sufficient size and quality to obtain useful information about the structural properties of GR and molecules or complexes that may associate with GR.

In one embodiment, a composition is provided that comprises a protein in crystalline form wherein at least a portion of the protein has 55%, 65%, 75%, 85%, 90%, 95%, 97%, 99% or greater identity with residues 528-777 of SEQ. ID No. 1.

In one variation, the protein has activity characteristic of GR. For example, the protein may optionally be inhibited by inhibitors of wild type GR. The protein crystal may also diffract X-rays for a determination of structure coordinates to a resolution of 4 Å, 3.5 Å, 3.0 Å or less.

In one variation, the protein crystal has a crystal lattice in a $P2_12_12$ space group. The protein crystal may also have a crystal lattice having unit cell dimensions, +/−5%, of a=202.02 Å, b=110.31 Å and c=116.62 Å, $\alpha=\beta=\gamma=90$.

The present invention is also directed to crystallizing GR. The present invention is also directed to the conditions useful for crystallizing GR. It should be recognized that a wide variety of crystallization methods can be used in combination with the crystallization conditions to form crystals comprising GR including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 528-777 of SEQ. ID No. 1; and storing the crystallization volume under conditions suitable for crystal formation.

In one variation, the crystallization volume comprises the protein in a concentration between 1 mg/mL and 50 mg/mL, and 5-50% w/v of precipitant wherein the precipitant comprises one or more members of the group consisting of PEG having a molecular weight range between 200-20000 and wherein the crystallization volume has a pH between pH4 and pH10.

In another variation, the crystallization volume comprises the protein in a concentration between 1 mg/mL and 50 mg/mL, and 5-50% w/v of precipitant wherein the precipitant comprises one or more members of the group consisting of 0.2-4.0M ammonium formate, sodium phosphate, potassium phosphate or ammonium phosphate and wherein the crystallization volume has a pH between pH4 and pH10.

The method may optionally further comprise forming a protein crystal that has a crystal lattice in a $P2_12_12$ space group. The method also optionally further comprises forming a protein crystal that has a crystal lattice having unit cell dimensions, +/−5%, of a=202.02 Å, b=110.31 Å and c=116.62 Å, $\alpha=\beta=\gamma=90$. The invention also relates to protein crystals formed by these methods.

The present invention is also directed to a composition comprising an isolated protein that comprises or consists of one or more of the protein sequence(s) of GR taught herein for crystallizing GR. The present invention is also directed to a composition comprising an isolated nucleic acid molecule that comprises or consists of the nucleotides for expressing the protein sequence of GR taught herein for crystallizing GR.

The present invention is also directed to an expression vector that may be used to express the isolated proteins taught herein for crystallizing GR. In one variation, the expression vector comprises a promoter that promotes expression of the isolated protein.

The present invention is also directed to a cell line transformed or transfected by an isolated nucleic acid molecule or expression vector of the present invention.

In regard to each of these embodiments, the protein may optionally have activity characteristic of GR. For example, the protein may optionally be inhibited by inhibitors of wild type GR.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 528-777 of SEQ. ID No. 1; and performing rational drug design using a three dimensional structure that is based on the obtained structure coordinates.

The protein crystals may optionally have a crystal lattice with a $P2_12_12$ space group and unit cell dimensions, +/−5%, of a=202.02 Å, b=110.31 Å and c=116.62 Å, $\alpha=\beta=\gamma=90$.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

DETAILED DESCRIPTION OF THE INVENTION

The present invention relates to a member of a family of nuclear hormone receptors and more specifically to Glucocorticoid Receptor (GR). Provided are GR in crystalline form, methods of forming crystals comprising GR, and methods of using crystals comprising GR.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

It will be readily apparent to those of skill in the art that the numbering of amino acids in other isoforms of GR may be different than that set forth for GR. Corresponding amino acids in other isoforms of GR are easily identified by visual inspection of the amino acid sequences or by using commercially available homology software programs, as further described below.

1. GR

Glucocorticoids are steroid hormones that participate in many physiological processes including endocrine homeostasis, stress response, lipid metabolism, inflammation and apoptosis. These actions are mediated by the intracellular glucocorticoid receptor (GR) which belongs to the nuclear receptor (NR) superfamily. GR is a steroid hormone-activated transcriptional factor known to regulate target genes involved in glucose homeostasis, bone turnover, cell differentiation, lung maturation and inflammation. GR is an important therapeutic target with dexamethasone and other related corticosteroid analogs used to treat conditions including, but not limited to, asthma, rheumatoid arthritis, allergic rhinitis and leukemia, but clinical use of these corticosteroids is limited by a number of deleterious side effects. Hence, compounds are being developed that act as GR agonists with strong anti-inflammatory activity but without the undesirable side effects.

GR is a multi-domain protein consisting of an amino-terminal activation function-1 domain (AF-1), a DNA-binding domain and a carboxy-terminal ligand binding domain (LBD). Hormone or ligand binding to the GR ligand binding domain activates the cytoplasmic receptor, inducing dimer formation and transfer of GR into the nucleus, where it binds to promoters in the DNA and either activates or represses transcription of specific genes. The LBD also contains a ligand-dependent activation function (AF-2) helix that assumes an active conformation upon ligand binding and facilitates binding of co-activator proteins, including the transcriptional intermediary factor 2 (TIF2). As such, co-crystal structures of GR bound to specific compounds and TIF2 activator peptides are of increasing interest for elucidating the structural basis of emerging pharmaceuticals that target GR mediated cellular responses.

Figure 1:
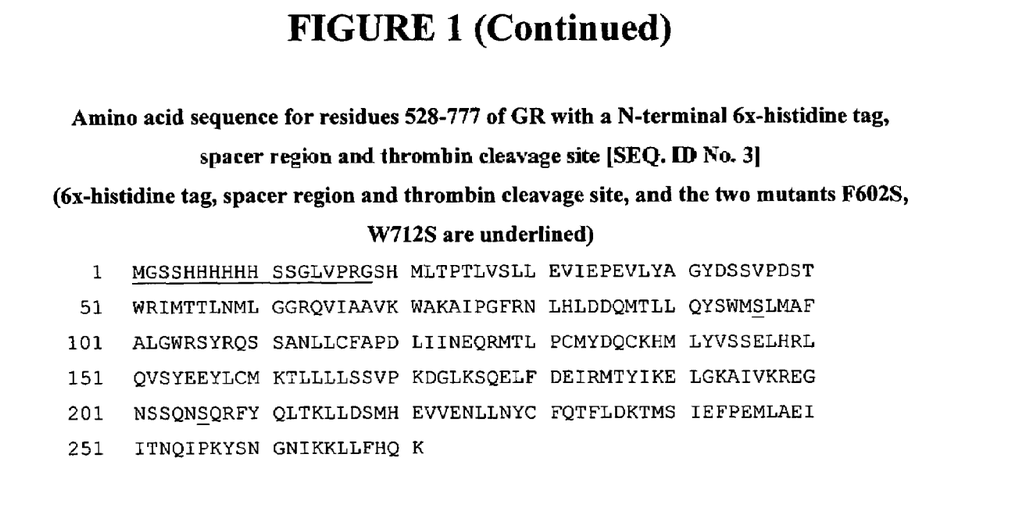
FIG. 1 illustrates SEQ. ID Nos. 1, 2, and 3 referred to in this application.

In one embodiment, GR comprises the wild-type form of the full length GR, set forth herein as SEQ. ID No. 1 (GenBank Accession Number NM_000222; Hollenberg, S. M., Weinberger, C., Ong, E. S., Cerelli, G., Oro, A., Lebo, R., Thompson, E. B., Rosenfeld, M. G. and Evans, R. M., "Primary structure and expression of a functional human glucocorticoid receptor cDNA," Nature 318 (6047), 635-641 (1985).

In another embodiment, GR comprises residues 528-777 of SEQ. ID No. 1 which comprises the active site domain of wild-type GR. The "active site binding pockets" or "active site" of GR refers to the area on the surface of GR where the substrate binds.

It should be recognized that the invention may be readily extended to various variants of wild-type GR and variants of fragments thereof. In another embodiment, GR comprises a sequence wherein at least a portion of the sequence has 55%, 65%, 75%, 85%, 90%, 95%, 97%, 99% or greater identity with SEQ. ID No. 1.

It is also noted that the above sequences of GR are also intended to encompass isoforms, mutants and fusion proteins of these sequences. An example of a fusion protein is provided by SEQ. ID No. 3, which includes a 6 residue N-terminal tag (6 residues are histidine), a spacer region and a thrombin cleavage site that may be used to facilitate purification of the protein. SEQ. ID No. 3 also contains mutations at residues 602 (i.e., F602S) and 712 (i.e., W712S).

A wide variety of GR variants (e.g., insertions, deletions, substitutions, etc.) that fall within the above specified identity ranges may be designed and manufactured utilizing recombinant DNA techniques well known to those skilled in the art. These modifications can be used in a number of combinations to produce the variants. The present invention is useful for crystallizing and then solving the structure of the range of variants of GR.

Variants of GR may be insertional variants in which one or more amino acid residues are introduced into a predetermined site in the GR sequence. For instance, insertional variants can be fusions of heterologous proteins or polypeptides to the amino or carboxyl terminus of the subunits.

Variants of GR also may be substitutional variants in which at least one residue has been removed and a different residue inserted in its place. An example of a substitutional variant is provided by SEQ. ID No. 3, which includes mutations at residues 602 (i.e., F602S) and 712 (i.e., W712S). Non-natural amino acids (i.e., amino acids not normally found in native proteins), as well as isosteric analogs (amino acid or otherwise), may optionally be employed in substitutional variants. Examples of suitable substitutions are well known in the art, such as Glu→Asp, Asp→Glu, Ser→Cys, and Cys→Ser for example.

Another class of variants is deletional variants, which are characterized by the removal of one or more amino acid residues from the GR sequence.

Other variants may be produced by chemically modifying amino acids of the native protein (e.g, diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution with bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea; 2,4-pentanedione; transaminase catalyzed reaction with glyoxylate; and N-hydroxysuccinamide esters of polyethylene glycol or other bulky substitutions.

Arginyl residues may be modified by reaction with a number of reagents, including phenylglyoxal; 2,3-butanedione; 1,2-cyclohexanedione; and ninhydrin. Modification of arginine residues requires that the reaction be performed in alkaline conditions because of the high $pK_a$ of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding GR may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for there affect on a variety of different properties including, for example, solubility, crystallizability and a modification to the protein's structure and activity.

In one variation, the variant and/or fragment of wild-type GR is functional in the sense that the resulting protein is capable of associating with at least one same chemical entity that is also capable of selectively associating with a protein comprising the wild-type GR (e.g., residues 528-777 of SEQ. ID No. 1) since this common associative ability evidences that at least a portion of the native structure has been conserved.

It is noted that the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of GR, and the atomic structure coordinates obtained therefrom, can be used to identify compounds that bind to the native domain. These compounds may affect the activity of the native domain.

Amino acid substitutions, deletions and additions that do not significantly interfere with the three-dimensional structure of GR will depend, in part, on the region where the substitution, addition or deletion occurs in the crystal structure. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine; isoleucine; valine; glycine; alanine; asparagine; glutamine; serine; threonine; phenylalanine; and tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of GR will be apparent to those having skills in the art.

2. Cloning, Expression and Purification of GR

The gene encoding GR can be isolated from RNA, cDNA or cDNA libraries. In this case, the portion of the gene encoding amino acid residues 528-777 (SEQ. ID No. 1), corresponding to <DESCRIBE PROTEIN>, was isolated and is shown as SEQ. ID No. 2.

The gene encoding GR can be isolated from RNA, cDNA or cDNA libraries. In this case, the portion of the gene encoding amino acid residues 528-777 (SEQ ID NO:1), corresponding to the active site domain of wild-type GR, was isolated and is shown as SEQ ID NO:2.

A variety of expression systems and hosts may be used for the expression of GR. Example 1 provides one such expression system.

Once expressed, purification steps are employed to produce GR in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

GR may optionally be affinity labeled during cloning, preferably with a N-terminal six-histidine tag and thrombin cleavage site, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization and Crystals Comprising GR

One aspect of the present invention relates to methods for forming crystals comprising GR as well as crystals comprising GR.

In one embodiment, a method for forming crystals comprising GR is provided comprising forming a crystallization volume comprising GR, one or more precipitants, optionally a buffer, optionally a monovalent and/or divalent salt and optionally an organic solvent; and storing the crystallization volume under conditions suitable for crystal formation.

In yet another embodiment, a method for forming crystals comprising GR is provided comprising forming a crystallization volume comprising GR in solution comprising the components shown in Table 1; and storing the crystallization volume under conditions suitable for crystal formation.

TABLE 1

Precipitant 5-50% w/v of precipitant wherein the precipitant comprises one or more members of the group consisting of PEG MME having a molecular weight range between 1000-10000, PEG having a molecular weight range between 100-10000, and 0.2-4.0M Ammonium formate or Sodium, potassium or ammonium phosphate.

pH pH 4-10. Buffers that may be used include, but are not limited to tris, bicine, phosphate, cacodylate, acetate, citrate, HEPES, PIPES, MES and combinations thereof.

Additives

Optionally 0.05 to 2.5M additives wherein the additives comprise a monovalent and/or divalent salt (for example, sodium, lithium, magnesium, calcium, and the like)

Protein Concentration 1 mg/mL-50 mg/mL

Temperature

1° C.-25° C.

In yet another embodiment, a method for forming crystals comprising GR is provided comprising forming a crystallization volume comprising GR; introducing crystals comprising GR as nucleation sites; and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro, macro and/or streak seeding of crystals may also be performed to facilitate crystallization.

It should be understood that forming crystals comprising GR and crystals comprising GR according to the invention are not intended to be limited to the wild type, full length GR ligand binding domain shown in SEQ. ID No. 1 and fragments comprising residues 528-777 of SEQ. ID No. 1. Rather, it should be recognized that the invention may be extended to various other fragments and variants of wild-type GR as described above.

It should also be understood that forming crystals comprising GR and crystals comprising GR according to the invention may be such that GR is optionally complexed with one or more ligands and one or more copies of the same ligand. The ligand used to form the complex may be any ligand capable of binding to GR. In one variation, the ligand is a natural substrate. In another variation, the ligand is an inhibitor.

In one particular embodiment, GR crystals have a crystal lattice in the $P2_12_12$ space group. GR crystals may also optionally have unit cell dimensions, +/−5%, of a=202.02 Å, b=110.31 Å and c=116.62 Å, $\alpha=\beta=\gamma 90$. GR crystals also preferably are capable of diffracting X-rays for determination of atomic coordinates to a resolution of 4 Å, 3.5 Å, 3.0 Å or better.

Crystals comprising GR may be formed by a variety of different methods known in the art. For example, crystallizations may be performed by batch, dialysis, and vapor diffusion (sitting drop and hanging drop) methods. A detailed description of basic protein crystallization setups may be found in McRee, D., *Practical Protein Crystallography*, $2^{nd}$ Ed. (1999), Academic Press Inc. Further descriptions regarding performing crystallization experiments are provided in Stevens et al. (2000) *Curr. Opin. Struct. Biol.*: 10(5):558-63, and U.S. Pat. Nos. 6,296,673; 5,419,278; and 5,096, 676.

In one variation, crystals comprising GR are formed by mixing substantially pure GR with an aqueous buffer containing a precipitant at a concentration just below a concentration necessary to precipitate the protein. One suitable precipitant for crystallizing GR is polyethylene glycol (PEG), which combines some of the characteristics of the salts and other organic precipitants (see, for example, Ward et al., J. Mol. Biol. 98:161, 1975, and McPherson, J. Biol. Chem. 251:6300, 1976). Another suitable precipitant for crystallizing GR is ammonium formate.

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a GR complex were obtained. In order to accomplish this, systematic broad screen crystallization trials were performed on a GR complex using the sitting drop technique. In each experiment, a 100 nL mixture of GR complex and precipitant was placed on a platform positioned over a well containing 100 μL of the precipitating solution. Precipitate and crystal formation was detected in the sitting drops. Fine screening was then carried out for those crystallization conditions that appeared to produce precipitate and/or crystal in the drops.

Figure 2:
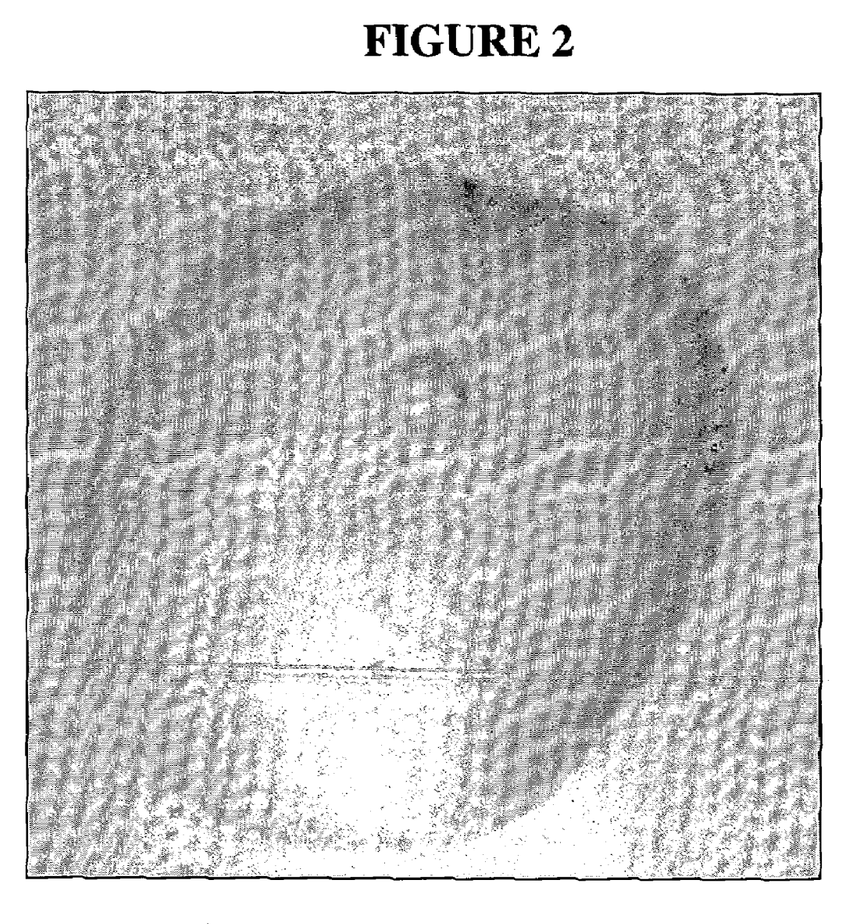
FIG. 2 illustrates a crystal of GR corresponding to SEQ. ID No. 3, having a crystal lattice in a $P2_12_12$ space group and unit cell dimensions, +/−5%, of a=202.02 Å, b=110.31 Å and c=116.62 Å, $\alpha=\beta=\gamma=90$.

Based on the crystallization experiments that were performed, a thorough understanding of how different crystallization conditions affect GR crystallization was obtained. Based on this understanding, a series of crystallization conditions were identified that may be used to form crystals comprising GR. These conditions are summarized in Table 1. A particular example of crystallization conditions that may be used to form diffraction quality crystals of the GR complex is detailed in Example 2. FIG. 2 illustrates crystals of the GR complex formed using the crystallization conditions provided in Table 1.

One skilled in the art will recognize that the crystallization conditions provided in Table 1 and Example 2 can be varied and still yield protein crystals comprising GR. For example, it is noted that variations on the crystallization conditions described herein can be readily determined by taking the conditions provided in Table 1 and performing fine screens around those conditions by varying the type and concentration of the components in order to determine additional suitable conditions for crystallizing GR, variants of GR, and ligand complexes thereof.

Crystals comprising GR have a wide range of uses. For example, now that crystals comprising GR have been produced, it is noted that crystallizations may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising GR according to the present invention, the crystals so formed can be used by this crystallization technique to initiate crystal growth of other GR comprising crystals, including GR complexed to other ligands.

As will be described herein in greater detail, crystals may also be used to perform X-ray or neutron diffraction analysis in order to determine the three-dimensional structure of GR and, in particular, to assist in the identification of its active site. Knowledge of the binding site region allows rational design and construction of ligands including inhibitors.

Crystallization and structural determination of GR mutants having altered bioactivity allows the evaluation of whether such changes are caused by general structure deformation or by side chain alterations at the substitution site.

4. X-Ray Data Collection and Structure Determination

Crystals comprising GR may be obtained as described above in Section 3. As described herein, these crystals may then be used to perform X-ray data collection and for structure determination.

In one embodiment, described in Example 2, crystals of GR were obtained where GR has the sequence of residues shown in SEQ. ID No. 3. These particular crystals were used to determine the three dimensional structure of the GR ligand binding domain. However, it is noted that other crystals comprising GR including different GR variants, fragments, and complexes thereof may also be used.

Diffraction data were collected from cryocooled crystals (100K) of GR at the Advanced Light. Source (ALS) beam line 5.0.3 using an ADSC Quantum CCD detector. The diffraction pattern of the GR crystals displayed symmetry consistent with space group $P2_12_12$ with unit cell dimensions a=202.02 Å, b=110.31 Å and c=116.62 Å, $\alpha=\beta=\gamma=90$ (+/−5%). Data were collected and integrated to 2.49 Å with the HKL2000 program package (Otwinowski, Z. and Minor, W., *Meth. Enzymol.* 276:307 (1997)).

The X-ray diffraction data collection statistics are given in Table 2.

TABLE 2

| Crystal data | | |
|---|---|---|
| Space group | | $P2_12_12$ |
| Unit cell dimensions | | a = 202.02Å |
| | | b = 110.31Å |
| | | c = 116.62Å |
| Data collection | | |
| X-ray source | | ALS BL 5.0.3 |
| Wavelength [Å] | | 1.00 |
| Resolution [Å] | | 2.49 |
| Observations (unique) | | 85130 |
| Redundancy | | 3.27 |
| Completeness | overall (outer shell) | 93.4 (94.2)% |
| I/σ(I) | overall (outer shell) | 18.5 (3.2) |
| $R_{symm}^1$ | overall (outer shell) | 0.038 (.377) |

Based on crystal volume calculations, where the unit cell dimensions were a=202.02 Å, b=110.31 Å and c=116.62 Å, $\alpha=\beta=\gamma=90$, it was realized that the asymmetric unit comprised six GR molecules.

5. Uses of the Crystal and Diffraction Pattern of GR

Crystals, crystallization conditions and the diffraction pattern of GR that can be generated from the crystals also have a range of uses. One particular use relates to screening entities that are not known ligands of GR for their ability to bind to GR. For example, with the availability of crystallization conditions, crystals and diffraction patterns of GR provided according to the present invention, it is possible to take a crystal of GR; expose the crystal to one or more entities that may be a ligand of GR; and determine whether a ligand/GR complex is formed. The crystals of GR may be exposed to potential ligands by various methods, including but not limited to, soaking a crystal in a solution of one or more potential ligands or co-crystallizing GR in the presence of one or more potential ligands.

Once one or more ligands are identified, structural information from the ligand/GR complex(es) may be used to design new ligands that bind tighter, bind more specifically, have better biological activity or have better safety profiles than known ligands.

In one embodiment, a method is provided for identifying a ligand that binds to GR comprising: (a) attempting to crystallize a protein that comprises a sequence wherein at least a portion of the sequence has 55%, 65%, 75%, 85%, 90%, 95%, 97%, 99% or greater identity with SEQ. ID No. 3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to GR comprising: soaking a crystal of a protein wherein at least a portion of the protein has 55%, 65%, 75%, 85%, 90%, 95%, 97%, 99% or greater identity with SEQ. ID No. 3 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-GR complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

According to another embodiment, the invention provides compounds that associate with a GR-like binding pocket produced or identified by various methods set forth above. The terms "binding site" or "binding pocket", as used herein, refer to a region of a protein that, as a result of its shape, favorably associates with a ligand or substrate. Similarly, the term "GR-like binding pocket" refers to a portion of a molecule or molecular complex whose shape is sufficiently similar to the GR binding pockets as to bind common ligands. This commonality of shape may be quantitatively defined based on a comparison to a reference point (e.g., a set of structure coordinates). For example, the commonality of shape may be quantitatively defined based on a root mean square deviation (RMSD) from the structure coordinates of the backbone atoms of the amino acids that make up the binding pockets in GR).

EXAMPLES

Example 1

Expression and Purification of GR

This example describes cloning, expression and purification of the GR ligand binding domain with the point mutations F602S and W712S. It should be noted that a variety of other expression systems and hosts are also suitable for the expression of GR, as would be readily appreciated by one of skill in the art.

The portion of the gene encoding residues 528-777 (from SEQ. ID No. 1), which corresponds to the ligand binding domain of human GR, was cloned into a modified pET15b vector at the NdeI and BamHI sites (Novagen). Expression from this vector produced the recombinant GR ligand binding domain with a 6x-histidine tag at the N-terminus followed by a thrombin cleavage site to facilitate purification and tag removal (the excised 6x-Histidine tag and thrombin cleavage site sequences are underlined in SEQ. ID No. 3). Point mutations F602S and W712S were introduced using a standard site-specific mutagenesis protocol. All cloning and mutagenesis experiments were conducted using DH10B-1r. The pET15b plasmid containing GR (residues 528-777, F602S, W712S) was transformed into the *E. coli* strain BL21-AI (Invitrogen).

Passage *E. coli* strain BL21-AI harboring pET15b vector containing GR (residues 528-777, F602S, W712S) was grown overnight in LB medium overnight ampicillin. Six 2-liter flasks each containing 1-liter of LB media were inoculated with overnight culture at 1/100 dilution. Cells were grown at 37° C., 220 rpm to an $OD_{600}$ of approximately 0.5 at which time Dexamethasone (20 mM solution in ethanol) was added to cells at 500 µM final concentration and cells were transferred to a 25° C. shaker for 30 minutes prior to induction with 0.2% arabinose and 1 mM IPTG for approximately 21 hours. The cells were harvested by centrifugation and the cells stored at −80° C. until required. Frozen cells from six 1-liter cultures grown in shake flasks were removed from the −80° C. freezer and thawed by addition of 30 mL of Lysis buffer (50 mM Tris-HCl, pH 7.9, 50 mM NaCl, 1 mM $MgCl_2$, 40 µM Dexamethasone containing hen egg white lysozyme (0.6 mg/mL) and Benzonase (2.5 U/mL)). Lysed cells were allowed to stand for 30 minutes at 4° C. and sonicated at approximately 12 W for 4×30 seconds using a microtip Vibra Cell apparatus (Sonic model VCX-750). Lysate was clarified by centrifugation at 16,000×g for 30 minutes at 4° C. Clarified lysate was pooled and ATP and $MgCl_2$ were added to 10 mM and 20 mM concentration, respectively. Clarified lysate was incubated at 37° C. for 10 minutes and 3.5 mg of denatured *E. coli* protein was added per 180 mL of clarified lysate. Clarified lysate was allowed to incubate for an additional 20 min at 37° C. Precipitated material was removed by centrifugation at 16,000×g for 30 min at 4° C. The supernatants were pooled and applied to a 3 mL ProBond (Invitrogen) resin that had been equilibrated with 50 mM potassium phosphate, pH 7.8, 400 mM NaCl, 100 mM KCl, 20 mM Imidazole, 10% glycerol, and 50 µM Dexamethasone. The column was washed with at least 20 column volumes of 50 mM potassium phosphate, pH 7.8, 400 mM NaCl, 100 mM KCl, 40 mM Imidazole, 10% glycerol, 50 µM Dexamethasone. GR (residues 528-777, F602S, W712S) was eluted with 4 column volumes of 50 mM potassium phosphate, pH 7.4, 400 mM NaCl, 100 mM KCl, 200 mM Imidazole, 10% glycerol, 10 mM 1,4-Dithio-DL-threitol, and 50 µM Dexamethasone. Fractions containing purified GR (residues 528-777, F602S, W712S) were pooled and assayed for protein concentration. If necessary, additional Dexamethasone was added to the fractions to maintain the 1:10 protein:ligand ratio, and then diluted 10-fold with Delivery Buffer (25 mM Tris-HCl, pH 8.5, 50 mM NaCl, 3% glycerol, 10 mM 1,4-Dithio-DL-threitol, 50 µM Dexamethasone). Two-fold molar excess of TIF2 peptide (sequence KQEPVSPKKKENALLRYLLD-KDDTK (SEQ. ID No. 4)) was added to the diluted protein solution and incubated at 4° C. for a minimum of 1 hour prior to concentrating the sample to around 25 mg/mL. The purified protein was monomeric by analytical size-exclusion chromatography and exhibited a major band by sodium-dodecyl-sulfate polyacrylamide gel electrophoresis (SDS-PAGE) analysis for GR (residues 528-777, F602S, W712S) and a major band for the TIF2 peptide.

Example 2

Crystallization of GR

This example describes the crystallization of GR. It is noted that the precise crystallization conditions used may be further varied, for example by performing a fine screen based on these crystallization conditions.

GR protein samples (corresponding to SEQ. ID No. 3) containing Dexamethasone and TIF2 peptide were used for crystallization trials. Crystals were obtained after an extensive and broad screen of conditions, followed by optimization. Diffraction quality crystals were grown in 100 nL sitting droplets using the vapor diffusion method. 50 nL comprising the GR-complex (25 mg/mL) was mixed with 50 nL from a reservoir solution (100 µl) comprising: 2.4M ammonium formate and 0.1M HEPES buffer pH=7.6. The resulting solution was incubated over a period of one week at 4° C. Crystals typically appeared after 3-5 days and grew to a maximum size within 7-10 days. Single crystals were transferred, briefly, into a cryoprotecting solution containing the reservoir solution supplemented with 25% v/v glycerol. Crystals were then flash frozen by immersion in liquid nitrogen and then stored under liquid nitrogen. A crystal of the GR-complex produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, patent applications, papers, and books cited in this application are incorporated herein in their entirety.

---

We claim:

1. A composition comprising a protein in crystalline form wherein the protein consists of SEQ ID NO:3, wherein said proteins forms a complex with a steroid ligand, and wherein the protein crystal has a crystal lattice in a P2$_1$2$_1$2 space group and unit cell dimensions, +/−5%, of a=202.02 Å, b=110.31 Å and c=116.62 Å, α=β=γ=90.

2. A composition according to claim 1 wherein the crystal diffracts X-rays for a determination of structure coordinates to a resolution of a value equal to or less than 3.0 Angstroms.

3. A method for forming a crystal of a protein comprising:
forming a crystallization volume comprising: a precipitant solution and a protein that consists of SEQ ID NO:3, wherein said proteins forms a complex with a steroid ligand, and wherein the protein crystal has a crystal lattice in a $P2_12_12$ space group and unit cell dimensions, +/−5%, of a=202.02 Å, b=110.31 Å and c=116.62 Å, $\alpha=\beta=\gamma=90$, and
storing the crystallization volume under conditions suitable for crystal formation of the protein.

4. A method according to claim 3 wherein the crystal diffracts X-rays for a determination of structure coordinates to a resolution of a value equal to or less than 3.0 Angstroms.

5. A method according to claim 3, the method further comprising diffracting the protein crystal to produce a diffraction pattern.

6. An isolated soluble protein consisting of residues 528-777 of SEQ ID NO:1.

7. The protein according to claim 6 wherein the protein is expressed from a nucleic acid molecule that consists of SEQ ID NO:2.

8. A soluble protein consisting of SEQ ID NO:3.

9. An isolated non-crystalline protein consisting of amino acids 528-777 of SEQ ID NO:1.

* * * * *

SEQUENCE LISTING

```
<160> NUMBER OF SEQ ID NOS: 4

<210> SEQ ID NO 1
<211> LENGTH: 777
<212> TYPE: PRT
<213> ORGANISM: Homo sapien
<220> FEATURE:
<221> NAME/KEY: MISC_FEATURE
<223> OTHER INFORMATION: Amino acid sequence for human Glucocorticoid
      Receptor

<400> SEQUENCE: 1

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205
```

```
Asn Glu Ser Pro Trp Arg Ser Asp Leu Leu Ile Asp Glu Asn Cys Leu
210                 215                 220

Leu Ser Pro Leu Ala Gly Glu Asp Ser Phe Leu Leu Glu Gly Asn
225             230              235                 240

Ser Asn Glu Asp Cys Lys Pro Leu Ile Leu Pro Asp Thr Lys Pro Lys
            245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
            435                 440                 445

Val Glu Gly Gln His Asn Tyr Leu Cys Ala Gly Arg Asn Asp Cys Ile
450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
            565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
```

```
                625              630              635              640

Asp Gln Cys Lys His Met Leu Tyr Val Ser Ser Glu Leu His Arg Leu
                    645              650              655

Gln Val Ser Tyr Glu Glu Tyr Leu Cys Met Lys Thr Leu Leu Leu Leu
                660              665              670

Ser Ser Val Pro Lys Asp Gly Leu Lys Ser Gln Glu Leu Phe Asp Glu
                    675              680              685

Ile Arg Met Thr Tyr Ile Lys Glu Leu Gly Lys Ala Ile Val Lys Arg
            690              695              700

Glu Gly Asn Ser Ser Gln Asn Trp Gln Arg Phe Tyr Gln Leu Thr Lys
705              710              715              720

Leu Leu Asp Ser Met His Glu Val Val Glu Asn Leu Leu Asn Tyr Cys
                    725              730              735

Phe Gln Thr Phe Leu Asp Lys Thr Met Ser Ile Glu Phe Pro Glu Met
                740              745              750

Leu Ala Glu Ile Ile Thr Asn Gln Ile Pro Lys Tyr Ser Asn Gly Asn
                    755              760              765

Ile Lys Lys Leu Leu Phe His Gln Lys
            770              775

<210> SEQ ID NO 2
<211> LENGTH: 751
<212> TYPE: DNA
<213> ORGANISM: Homo sapien
<220> FEATURE:
<221> NAME/KEY: misc_feature
<223> OTHER INFORMATION: Human cDNA sequence encoding residues 528-777
      of GR

<400> SEQUENCE: 2 ctcacccta  ccctggtgtc  actgttggag  gttattgaac  ctgaagtgtt  atatgcagga      60
tatgatagct ctgttccaga  ctcaacttgg  aggatcatga  ctacgctcaa  catgttagga     120
gggcggcaag tgattgcagc  agtgaaatgg  gcaaaggcaa  taccaggttt  caggaactta     180
cacctggatg accaaatgac  cctactgcag  tactcctgga  tgtttcttat  ggcatttgct     240
ctggggtgga gatcatatag  acaatcaagt  gcaaacctgc  tgtgttttgc  tcctgatctg     300
attattaatg agcagagaat  gactctaccc  tgcatgtacg  accaatgtaa  acacatgctg     360
tatgtttcct ctgagttaca  caggcttcag  gtatcttatg  aagagtatct  ctgtatgaaa     420
accttactgc ttctctcttc  agttcctaag  gacggtctga  agagccaaga  gctatttgat     480
gaaattagaa tgacctacat  caaagagcta  ggaaaagcca  ttgtcaagag  ggaaggaaac     540
tccagccaga actggcagcg  gttttatcaa  ctgacaaaac  tcttggattc  tatgcatgaa     600
gtggttgaaa atctccttaa  ctattgcttc  caaacatttt  tggataagac  catgagtatt     660
gaattccccg agatgttagc  tgaaatcatc  accaatcaga  taccaaaata  ttcaaatgga     720
aatatcaaaa aacttctgtt  tcatcaaaag  t                                     751

<210> SEQ ID NO 3
<211> LENGTH: 271
<212> TYPE: PRT
<213> ORGANISM: Artificial
<220> FEATURE:
<223> OTHER INFORMATION: Amino acid sequence for residues 528-777 of GR
      with an N-terminal 6x-histidine tag, spacer region and thrombin
      cleavage site and F602S and W712S mutations

<400> SEQUENCE: 3
```

```
Met Gly Ser Ser His His His His His Ser Ser Gly Leu Val Pro
1               5                   10                  15

Arg Gly Ser His Met Leu Thr Pro Thr Leu Val Ser Leu Leu Glu Val
                20              25              30

Ile Glu Pro Glu Val Leu Tyr Ala Gly Tyr Asp Ser Ser Val Pro Asp
            35              40              45

Ser Thr Trp Arg Ile Met Thr Thr Leu Asn Met Leu Gly Gly Arg Gln
        50              55              60

Val Ile Ala Ala Val Lys Trp Ala Lys Ala Ile Pro Gly Phe Arg Asn
65              70              75              80

Leu His Leu Asp Asp Gln Met Thr Leu Leu Gln Tyr Ser Trp Met Ser
            85              90              95

Leu Met Ala Phe Ala Leu Gly Trp Arg Ser Tyr Arg Gln Ser Ser Ala
                100             105             110

Asn Leu Leu Cys Phe Ala Pro Asp Leu Ile Ile Asn Glu Gln Arg Met
            115             120             125

Thr Leu Pro Cys Met Tyr Asp Gln Cys Lys His Met Leu Tyr Val Ser
    130             135             140

Ser Glu Leu His Arg Leu Gln Val Ser Tyr Glu Glu Tyr Leu Cys Met
145             150             155             160

Lys Thr Leu Leu Leu Leu Ser Ser Val Pro Lys Asp Gly Leu Lys Ser
                165             170             175

Gln Glu Leu Phe Asp Glu Ile Arg Met Thr Tyr Ile Lys Glu Leu Gly
            180             185             190

Lys Ala Ile Val Lys Arg Glu Gly Asn Ser Ser Gln Asn Ser Gln Arg
            195             200             205

Phe Tyr Gln Leu Thr Lys Leu Leu Asp Ser Met His Glu Val Val Glu
            210             215             220

Asn Leu Leu Asn Tyr Cys Phe Gln Thr Phe Leu Asp Lys Thr Met Ser
225             230             235             240

Ile Glu Phe Pro Glu Met Leu Ala Glu Ile Ile Thr Asn Gln Ile Pro
            245             250             255

Lys Tyr Ser Asn Gly Asn Ile Lys Lys Leu Leu Phe His Gln Lys
            260             265             270

<210> SEQ ID NO 4
<211> LENGTH: 25
<212> TYPE: PRT
<213> ORGANISM: Artificial
<220> FEATURE:
<223> OTHER INFORMATION: Amino acid sequence for TIF2 protein

<400> SEQUENCE: 4

Lys Gln Glu Pro Val Ser Pro Lys Lys Glu Asn Ala Leu Leu Arg
1               5                   10                  15

Tyr Leu Leu Asp Lys Asp Asp Thr Lys
                20              25
```